United States Patent [19]

Bridger

[11] 4,428,861

[45] Jan. 31, 1984

[54] MOLYBDENUM IV COMPOUNDS, PROCESS FOR PREPARATION THEREOF AND LUBRICANT COMPOSITIONS CONTAINING SAME

[75] Inventor: Robert F. Bridger, Hopewell, N.J.

[73] Assignee: Mobil Oil Corporation, New York, N.Y.

[21] Appl. No.: 314,290

[22] Filed: Oct. 23, 1981

Related U.S. Application Data

[63] Continuation-in-part of Ser. No. 115,456, Jan. 25, 1980, abandoned.

[51] Int. Cl.³ .............................................. C10M 1/48
[52] U.S. Cl. .............................................. 252/32.7 E
[58] Field of Search ............. 252/32.7 E, 46.7, 429 R, 252/429 K

[56] References Cited

U.S. PATENT DOCUMENTS

| | | | |
|---|---|---|---|
| 3,223,625 | 12/1965 | Cyphers et al. ....................... | 252/18 |
| 3,256,184 | 6/1966 | Harting et al. ................. | 252/32.7 R |
| 3,446,735 | 5/1969 | Wiese .............................. | 252/32.7 E |
| 4,175,043 | 11/1979 | Horodysky ...................... | 252/327 E |
| 4,208,292 | 6/1980 | Bridger .......................... | 252/32.7 E |
| 4,289,635 | 9/1981 | Schroeck ........................ | 252/32.7 E |

OTHER PUBLICATIONS

Newton et al., "Reactions of $Mo_2O_4^{2+}$ with Mercaptans and Implications for Molybdoenzymes", J.A.C.S., vol. 98, p. 5387, 1976.

*Primary Examiner*—Andrew Metz
*Attorney, Agent, or Firm*—Alexander J. McKillop; Michael G. Gilman; Howard M. Flournoy

[57] ABSTRACT

A novel process for reducing Mo(V) or Mo(VI) dialkyldithiophosphates to Mo(IV) dialkyldithiophosphates with $H_2S$ is provided. Homologues higher than the ethyl compound are oil soluble and novel. Lubricant compositions containing same provide reduced wear and friction.

23 Claims, No Drawings

MOLYBDENUM IV COMPOUNDS, PROCESS FOR PREPARATION THEREOF AND LUBRICANT COMPOSITIONS CONTAINING SAME

CROSS-REFERENCE TO RELATED APPLICATION

The present application is a continuation-in-part application of my co-pending application Ser. No. 115,456, filed on Jan. 25, 1980 for MOLYBDENUM IV COMPOUNDS, PROCESS FOR PREPARATION THEREOF AND LUBRICANT COMPOSITIONS CONTAINING SAME and now abandoned.

BACKGROUND OF THE INVENTION

1. Field of the Invention

This invention is directed to a novel process for preparing molybdenum (IV) dialkyldithiophosphates and to the novel oil-soluble compounds produced thereby and to lubricant compositions containing same.

2. Discussion of the Prior Art

The need for friction modifiers and antiwear agents in today's energy crisis is obvious. Such additives can significantly reduce fuel consumption in internal combustion engines. The use of molybdenum compound antiwear agents and friction modifiers is known in the art. U.S. Pat. No. 3,400,140 discloses the use of phosphomolybdates, U.S. Ser. No. 007,057, now U.S. Pat. No. 4,208,292, discloses phosphomolybdates prepared by reacting a dialkylphosphorodithioic acid with a metal of ammonium molybdate; it is also known that Mo(VI) compounds are effective as friction modifiers.

The reactions of oxomolybdenum complexes of bidentate sulfur ligands with hydrogen sulfide is a well known method for the preparation of sulfido molybdenum complexes via exchange of oxygen for sulfur. Such reactions have been applied routinely for the preparation of both terminal and bridging sulfido molybdenum complexes of dialkyldithiocarbamates (dtc); and dialkyldithiocarbonates (or xanthates, xan). W. E. Newton, J. L. Corbin and J. W. McDonald, *J. Amer. Soc.*, 98, 5387 (1976). Newton, McDonald, and co-workers, ibid, recently reinvestigated the reaction of a series of dioxo-bridged molybdenum(V) dialkyldithiocarbamates with hydrogen sulfide. They observed that sulfidation reactions occurred in a stepwise fashion, depending upon severity of reaction conditions, and that complete sulfidation required phosphorus pentasulfide as reactant.

Others have described sulfidation reactions using molybdenum(VI) dialkyldithiocarbamates of the type $MoO_2(dtc)_2$:

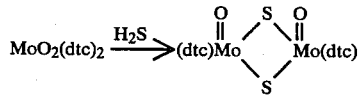

Accordingly the invention embodied herein is believed by applicants to be novel in all its aspects.

SUMMARY OF THE INVENTION

The present invention is directed to a novel process for preparing molybdenum(IV) dithiophosphates wherein molybdenum(V) or molybdenum(VI) dithiophosphates are reacted with hydrogen sulfide to produce molybdenum(IV) dithiophosphates of the type $MoO(dtp)_2$ where dtp is a dialkyldithiophosphato (or dialkylphosphorodithioato) ligand. The present invention is also directed to propyl or higher homologues as novel compounds and to antiwear/friction reducing lubricant compositions containing same.

In view of the above discussed prior art in general and particularly in view of the generality of the above referred to sulfido-oxo exchange reaction with bidentate sulfur ligands such as xanthate and dithiocarbamate, it is most surprising that the structurally similar oxomolybdenum dithiophosphates of the types $Mo_2O_3(dtp)_4$ and $MoO_2(dtp)_2$ do not give sulfido products when reacted with hydrogen sulfide. Instead, the molybdenum(IV) complex of the type $MoO(dtp)_2$, is the product.

Although the ethyl compound, $[(EtO)_2PS]_2MoO$, a known compound is insoluble in oil, the higher homologues, such as propyl, butyl and 2-ethylhexyl, possess better oil solubility and have not been reported in the literature. Therefore, the process described herein for the preparation of these compounds is novel, the lubricant compositions described herein are novel and the homologues higher than ethyl are also novel.

DESCRIPTION OF SPECIFIC EMBODIMENTS

Molybdenum(V) dithiophosphates of the type $Mo_2O_3(dtp)_4$ or molybdenum(VI) dithiophosphates of the type $MoO_2(dtp)_2$ are reacted with hydrogen sulfide to produce molybdenum(IV) dithiophosphates of the aforementioned $MoO(dtp)_2$:

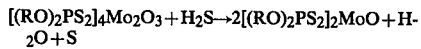

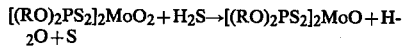

where dtp or $(RO)_2PS_2$ is a dialkyldithiophosphato (or dialkylphosphorodithioato) ligand. R is an alkyl group of from $C_1$ to about $C_{20}$.

The molybdenum(VI) compounds are generally prepared by reaction of a dihydrocarbyl- or preferably a dialkylphosphorodithioic acid with aqueous molybdenum(VI). The dihydrocarbyl- or dialkylphosphoric acid can be prepared for example by such prior art methods as reacting a monohydric alcohol with phosphorus pentasulfide.

Although the reactions of the present invention may conveniently take place under ambient conditions of temperature and pressure, it will be understood that these conditions may vary within wide limits. Accordingly, the reaction temperature may vary from about $-50°$ C. up to about $+50°$ C. and is preferably within the range of from about $-10°$ C. up to about $+30°$ C. The reaction pressure may also vary from about 7 psia up to about 70 psia and is preferably within the range of from about 14 psia up to about 30 psia.

The molybdenum(V) compounds may be prepared by reacting a metal, e.g., an alkali metal molybdate or an ammonium molybdate, such as ammonium hexamolybdate, with a dihydrocarbyl phosphorodithioic acid. As with the preparation of the molybdenum(VI) compounds hydrocarbyl includes alkyl, cycloalkyl, aryl or alkaryl and preferably containing from about 3 to 30 carbon atoms.

The base lubricants which are useful with the additives of this invention may be any oil of lubricating viscosity, whether natural, i.e., mineral, or synthetic. The natural oils include paraffinic, naphthenic and aromatic oils or mixtures of them. Among the synthetic oils are polyolefin (synthetic hydrocarbon) fluids, polyoxyalkylenes, polyacetals, polysiloxanes, polyesters and the like. The polyesters preferred are those made from polyhydric alcohols and monocarboxylic acids such as from pentaerythritol or neopentyl glycol and its homologues and aliphatic monocarboxylic acids having from 4 to 9 carbon atoms. Also useful are those polyesters made from polycarboxylic acids (e.g., sebacic acid) and monohydric alcohols (e.g., 2-ethylhexanol).

The base lubricant contemplated may also be a grease formulated by adding a grease-forming quantity of a thickening agent to one of the oils mentioned above. For this purpose a wide variety of materials may be employed. These thickening agents or gelling agents may include any of the conventional metal salts or soaps which are dispersed in the lubricating oil in grease-forming quantities in such degree as to impart to the resulting grease the desired consistency. Other thickening agents that may be employed in the formulation may comprise non-soap thickeners, such as modified clays and silicas, aryl ureas, calcium complexes and various other materials.

To achieve the purposes of this invention the lubricant compositions hereof should usually contain from about 0.01 to about 5 wt. % and more preferably from about 0.05 to 2 wt. % of the herein described molybdenum(IV) additive compounds. Any other lubricant additives may be also incorporated up to about 10 wt. % into said lubricant compositions for their known purposes.

Having described the invention in general terms, the following specific example is offered for purposes of illustration no intention to limit the invention thereby is to be inferred therefrom.

DESCRIPTION OF SPECIFIC EMBODIMENTS

EXAMPLE 1

Bis[O,O-di(2,2-dimethylpropyl)phosphorodithioato]oxomolybdenum(IV), $MoO(Me_2Prdtp)_2$. Excess hydrogen sulfide was introduced as a gas to a stirred solution of $MoO_2(Me_2Prdtp)_2$ (3 mmol, 2.0 g) in 30 ml chloroform at room temperature. The pale yellow solution turned maroon color after 2 to 3 minutes exposure to $H_2S$, changing at 9 min. to a dark green solution. The chloroform solution was evaporated in a stream of nitrogen and stored at 0° C. overnight to yield 0.5 g of pink solid. Repetition of this process yielded two further molybdenum-containing fractions for a total crude yield of 1.09 g (56%). Recrystallization from chloroform (64% recovery) under nitrogen gave a pink powder (1.07 mmol, 0.7 g) mp 176°–177° C., for a purified yield of 36% of $MoO(Me_2Prdtp)_2$. IR($CHCl_3$) dominated by ligand absorptions; $\gamma(Mo={}^{16}O)$ calcd. 970 cm$^{-1}$ from $\gamma(Mo={}^{18}O)$ 922 cm$^{-1}$. UV($CHCl_3$)$\gamma$, cm$^{-1}$(log.$_{10}\epsilon$): 39,800(3.71), 19,800(2.23), 16,000(sh. 1.63); spectra at 2 mM and 1.3 mM indicated that Beer's law was obeyed. $^{31}P$ NMR $(CDCl_3):\delta(^{31}P)134.5$; $^{17}O$ NMR $(CDCl_3):\delta(^{17}O)836,\Delta\gamma_{1/2}60$ Hz.

Anal. Calcd. for $C_{20}H_{44}MoO_5P_2S_4$: C, 36.92; H, 6.82; Mo, 14.74; P, 9.52; S, 19.71; mol wt., 651. Found: C, 36.83; H, 7.01; Mo, 15.01; P, 9.27; S, 19.39; mol wt. (vpo, $CHCl_3$)628.

Example 2

Bis[O,O-di(iso-propyl)phosphorodithioato]-oxomolybdenum(IV), $MoO(iPrdtp)_2$. The reaction of $Mo_2O_3(iPrdtp)_4$ (1.83 mmol, 2.0 g) in chloroform (30 ml) with hydrogen sulfide by the same procedure described in Example 1 gave 0.8 g (1.49 mmol, 41% yield) of $MoO(i-Prdtp)_2$, mp 133°–134° C. $^{31}P$ NMR $(CDCl_3):\delta(^{31}P)133.4$.

Anal. Calcd. for $C_{12}H_{28}O_5P_2S_4Mo$: C, 26.77; H, 5.24; P, 11.50; S, 23.82; Mo, 17.82. Found: C, 27.02; H, 5.25; P, 11.57; S, 23.96; Mo, 18.00.

Example 3

This example illustrates the preparation using large alkyl groups in the dithiophosphate moiety to impart better oil solubility. cis-Dioxobis[O,O-di(2-ethylhexyl)-phosphorodithioato]molybdenum(VI) (25 g, 0.03 mol) was treated at room temperature (without solvent) with a stream of hydrogen sulfide gas for 15 minutes. Hexane (50 ml) was added and the solution was treated with a vigorous stream of nitrogen to remove excess $H_2S$. The solution was filtered and solvent was removed by rotary evaporation to give 24 g of bis[O,O-di(2-ethylhexyl)-phosphorodithioato]oxomolybdenum(IV). The phosphorus-31 NMR resonance at $\delta$p135.9 indicated that the desired molybdenum(IV) compound was obtained.

Anal. Calcd. for $C_{32}H_{68}O_5P_2S_4Mo$: C, 46.93; H, 8.37; P, 7.56; S, 15.66; Mo, 11.71. Found: C, 49.13; H, 9.03; P, 6.62; S, 14.17; Mo, 10.79.

Example 4

M-Oxobis[oxobis-(O,O-diethylphosphorodithioato)-molybdenun(V)], $Mo_2O_3(Etdtp)_4$(0.0981 g, 0.1 mmol in 1 ml $CHCl_3$), was mixed with 2 ml $CHCl_3$ saturated with hydrogen sulfide. After 20 minutes at room temperature, a 77.5% yield (0.075 g) of bis(O,O-diethylphosphoro-dithioato)oxomolybdenum(IV), $MoO(Etdtp)_2$, was observed. Phosphorus-31 NMR $(CDCl_3):\delta(^{31}P)135.8$.

Example 5

Bis[O,O-di(n-butyl)phosphorodithioato]oxomolybdenum(IV), $MoO(n-Budtp)_2$, was prepared in 86% yield according to the procedure of Example 4. Phosphorus-31 NMR $(CDCl_3):\delta(^{31}P)133.5$.

Evaluation

Samples were evaluated as antiwear agents in a solvent refined paraffinic neutral Mid-Continental oil of 100 SUS at 100° F., 100 VI, 0° F. pour point, by using the Four Ball Wear Test.

WEAR TESTING METHOD

Additives were tested for antiwear activity using the Four Ball Wear Test, disclosed in U.S. Pat. No. 3,423,316. In general, in this test three steel balls of SAE 52100 steel are held in a ball cup. A fourth ball positioned on a rotable vertical axis is brought into contact with the three balls and is rotated against them. The force with which the fourth is held against the three stationary balls may be varied according to a desired load. The test lubricant is added to the ball cup and acts as a lubricant for the rotation. At the end of the test, the steel balls are investigated for wear scars; the extent of scarring represents the effectiveness of the lubricant as an antiwear agent. Results are also reported as wear rates in volume of wear per unit sliding distance per kilogram load. The lower the wear rate, the more effective the lubricant as an antiwear agent. The base stock oil employed in accordance with the test results shown in Table 1 comprised a 100 SUS at 100° F. solvent-refined paraffinic neutral oil of 0° F. pour point and 100

VI. Additives were evaluated at a concentration of 0.153% molybdenum in oil. Conditions of 40 Kg load, 600 rpm, and 30 minutes' test time were employed at 200° F.

TABLE 1

WEAR RESULTS OF MOLYBDENUM COMPOUNDS

| Example | Additive | Wt. % | Wear Scar Diameter, mm | Wear Rate × 10$^{13}$ |
|---|---|---|---|---|
| — | None (Base Lubricant) | — | 0.7728 | 76.3 |
| 1 | MoO(Me₂Prdtp)₂ | 1.04 | 0.4280 | 5.03 |
| 2 | MoO(iPrdtp)₂ | 0.86 | 0.3899 | 2.89 |
| 3 | MoO(2-EthHexdtp)₂ | 1.57 | 0.3759 | 2.26 |

The product of Example 3 was also tested as a friction reducer (mileage improver) in the Mobil Tecumseh Engine Test, developed by C. N. Rowe of the Mobil Research and Development Laboratory at Princeton, N.J. This test measures percent increase in RPM and increased power output at constant RPM of the engine over that of the test lubricant without the friction modifying additive. The test lubricant was Mobil 1.

DESCRIPTION OF ENGINE AND AUXILIARY EQUIPMENT

A 3.5 HP Tecumseh horizontal shaft engine was loaded by driving a 5 kw AC generator. The generator output was absorbed by two variable incadescent-light load banks.

Procedure

The engine is first flushed thoroughly with 1:1 toluene:Mobil SAE 10W and then normalized by repeated fill-run-drain cycles using the base oil for the next test sequences. An engine which is newly broken in is considered in a clean condition and the toluene/oil flush is omitted. The engine is started and warmed to a sump temperature of at least 70° C., keeping the RPM below 2200 by adjustment of throttle and/or load. Adjustment is then made so that power output is approximately 200 watts at about 2000 RPM. Recorder is started, and the apparatus allowed to run for one hour, or until a stable base line is attained. Should minor adjustments be required, these are followed by time necessary to insure stability of the system. All run parameters are recorded at this time.

The additive system to be evaluated is then introduced into the sump via a 25 cc hypodermic syringe, the needle being inserted through a septum replacing the oil fill plug. If the material to be evaluated is either solid or too viscous to inject, it is first dissolved in, or diluted with, a minimal quantity of base oil to facilitate handling. The engine is allowed to run for fifteen minutes, after which test parameters are noted for change. If RPM has increased, the load on the generator (light bank) is increased until the RPM returns to its original level. The new power output is noted. Percents increase in RPM and power output reflect the response of the additive. At no time is the throttle adjusted during the period of establishing the baseline for the base oil and the response of the additive.

As soon as the test is completed, the engine is shut-off, the additized oil drained and the engine is flushed several times with base oil.

TABLE 2

| TECUMSEH ENGINE TEST RESULTS | | | |
|---|---|---|---|
| Additive | Concentration Wt. % | % RPM Increase | % Output (Watts) Increase |
| Example 3 | 2.0 | 3.5 | 9.7 |

Although the present invention has been described with certain specific embodiments, it is to be understood that modifications and variations may be resorted to without departing from the spirit and scope of this invention as those skilled in the art will readily understand. Such modifications and variations are, of course, without the scope of the appended claims.

I claim:

1. A process for preparing bis(O,O-dialkylphosphorodithioato)oxomolybdenum(IV) compounds comprising reacting with H₂S a molybdenum(V) dithiophosphate or molybdenum(VI) dithiophosphate having the following respective general formulae:

[(RO)₂PS₂]₄Mo₂O₃ and

[(RO)₂PS₂]₂MoO₂ where R is a hydrocarbyl group having from 1 to 36 carbon atoms selected from alkyl, cycloalkyl, aryl or aralkyl and where the reaction is carried out in the presence of chloroform.

2. The process of claim 1 wherein (RO)₂PS₂ is a dialkylphorodithioato ligand.
3. The process of claim 2 wherein the alkyl group contains from 1 to about 30 carbon atoms.
4. The process of claim 2 wherein R is methylpropyl.
5. The process of claim 2 wherein R is isopropyl.
6. The process of claim 2 wherein R is 2-ethylhexyl.
7. The process of claim 2 wherein R is n-butyl.
8. A lubricant composition comprising a major amount of an oil of lubricating viscosity or a grease formulated therefrom and a minor amount sufficient to provide antiwear and friction reducing properties thereto of a compound prepared as described in claim 1.
9. The lubricant composition of claim 8 wherein (RO)₂PS₂ is a dialkylphosphorodithioato ligand.
10. The lubricant composition of claim 9 wherein the alkyl group of said ligand contains from 1 to 30 carbon atoms.
11. The lubricant composition of claim 9 wherein R is methylpropyl.
12. The lubricant composition of claim 9 wherein R is isopropyl.
13. The lubricant composition of claim 9 wherein R is 2-ethylhexyl.
14. A compound prepared by reacting with H₂S in the presence of chloroform a molybdenum(V) dithiophosphate or molybdenum(VI) dithiophosphate having the following respective general formulae:

[(RO)₂PS₂]₄Mo₂O₃ and

[(RO)₂PS₂]₂MoO₂ where R is a hydrocarbyl group having from 1 to 36 carbon atoms selected from alkyl, cycloalkyl, aryl or aralkyl and where the reaction is carried out in the presence of chloroform.

15. The compound of claim 14 wherein $(RO)_2PS_2$ is a dialkylphosphorodithioato ligand.

16. The compound of claim 15 wherein R is methylpropyl.

17. The compound of claim 15 wherein R is isopropyl.

18. The compound of claim 15 wherein R is 2-ethylhexyl.

19. The compound of claim 15 wherein R is n-butyl.

20. The process of claim 2 where R is 2,2-dimethylpropyl.

21. The lubricant composition of claim 9 wherein R is 2,2-dimethylpropyl.

22. The compound of claim 15 wherein R is 2,2-dimethylpropyl.

23. The lubricant composition of claim 9 wherein R is n-butyl.

* * * * *